United States Patent
Kawashima et al.

[11] Patent Number: 5,954,233
[45] Date of Patent: Sep. 21, 1999

[54] SEALED CONTAINER

[75] Inventors: Yoichi Kawashima, Kyoto, Japan; Daniel Sung-hwe Kim, Palo Alto, Calif.

[73] Assignee: Santen Pharmaceutical Co., Ltd., Japan

[21] Appl. No.: 09/123,868

[22] Filed: Jul. 28, 1998

[51] Int. Cl.⁶ ................................................. B67D 5/00
[52] U.S. Cl. ............................................. 222/83; 222/89
[58] Field of Search ............................ 222/81, 83, 83.5, 222/89

[56] References Cited

U.S. PATENT DOCUMENTS

| | | | |
|---|---|---|---|
| 3,840,136 | 10/1974 | Lanfranconi et al. | 222/83.5 X |
| 4,234,103 | 11/1980 | Strobl, Jr. et al. | 222/89 X |
| 4,296,786 | 10/1981 | Brignola | 222/83.5 X |
| 4,690,304 | 9/1987 | Morel | 222/83.5 X |
| 4,706,827 | 11/1987 | Cabernoch et al. . | |
| 4,722,449 | 2/1988 | Dubach | 222/83 X |
| 4,884,705 | 12/1989 | Debetencourt | 222/83 X |
| 4,982,875 | 1/1991 | Pozzi et al. | 222/83 |
| 5,004,127 | 4/1991 | Morel | 222/83 X |
| 5,020,690 | 6/1991 | Kishikawa et al. | 222/83 |
| 5,226,592 | 7/1993 | Pellerano | 222/83 |
| 5,388,690 | 2/1995 | Mutterle et al. | 222/83 X |
| 5,427,275 | 6/1995 | Hansen | 222/83 |
| 5,462,200 | 10/1995 | Weiler | 222/83 |
| 5,711,453 | 1/1998 | Weiler | 222/83 |
| 5,853,109 | 12/1998 | Elliott | 222/83 |

FOREIGN PATENT DOCUMENTS

| | | |
|---|---|---|
| 344686 | 9/1991 | Japan . |
| 2560817 | 10/1997 | Japan . |

*Primary Examiner*—Kevin P. Shaver
*Attorney, Agent, or Firm*—Webb Ziesenheim Logsdon Orkin & Hanson, P.C.

[57] ABSTRACT

A sealed container stores therein liquid such as eye drops in a sealed state. For dispensing the liquid first time, the factory-sealed outlet of the liquid is to be unsealed with a needled of a liquid discharge plug fitted within a cap in association with a user's operation of the cap in a loosening or tightening direction when the liquid is first dispensed therefrom. The container includes a one-way rotation preventing mechanism provided respectively at mutually opposing portions of a liquid discharge plug prefitted with the cap and the container. This mechanism prevents rotation of the liquid discharge plug in the loosening direction of the cap while allowing rotation thereof in the screwing direction of the cap when the cap has been tightened to a predetermined screwing position immediately before the needle initiates it penetrating action into the sealed liquid outlet. Also, a cam mechanism is provided respectively at mutually opposed positions of the discharge plug and the cap for pushing the liquid discharge plug toward the liquid outlet of the container body to a predetermined screwing position in association with the loosening operation of the cap under the rotation-restricted state provided by the one-way rotation preventing mechanism.

20 Claims, 8 Drawing Sheets

SEALED CONTAINER

BACKGROUND OF THE INVENTION

1. Field of the Invention

The present invention relates to a sealed container for holding therein liquid such as eye drops, cleaning solution for contact lens, the container having a container body with a liquid outlet thereof being factory-sealed for preventing or restricting contamination of the liquid by microorganisms or evaporation of the liquid before use, the liquid outlet being opened up to be communicated for use when penetrated in association with an operation of a cap.

2. Description of the Related Art

Containers of the above-noted type are known as follows (1)–(3).

(1) A container includes a container body storing liquid therein and having a factory-sealed liquid outlet and a cap detachably tightened on the container body. The cap forms, in its inner peripheral face, a female thread which is engageable with a male thread formed in an outer peripheral face of the container body. The cap also forms, in an inner bottom face thereof, a conical projection for penetrating the liquid outlet of the container body in association with a tightening (screwing) operation of the cap relative to the container body.

(2) A container includes a container body storing liquid therein and having a factory-sealed liquid outlet, a cap detachably tightened on the container body, a liquid discharge plug including a conical projection in the form of a needle capable of penetrating the liquid outlet of the container body and a discharge passage communicating between the inside and outside the container body through an inlet defined in an outer peripheral face of the projection, and a cap detachably fitted on the liquid discharge plug adjacent a peripheral edge of an exit of the discharge passage for sealing this discharge passage. The cap forms, in its inner peripheral face, a female thread which is engageable with a male thread formed in an outer peripheral face of the container body. In association with a tightening (screwing) operation of the cap relative to the container body, the conical projection of the liquid discharge plug is caused to advance for penetrating the sealed liquid outlet to allow discharge of the liquid for use (e.g. Japanese published utility model gazette No. 3-44686).

(3) A container includes a container body storing liquid therein and having a factory-sealed liquid outlet, a cap detachably tightened on the container body, a liquid discharge plug including a conical projection in the form of a needle capable of penetrating the liquid outlet of the container body and a discharge passage communicating between the inside and outside the container body through an inlet defined in an outer peripheral face of the projection, and a cap detachably fitted on the liquid discharge plug adjacent a peripheral edge of an exit of the discharge passage for sealing this discharge passage. The cap forms, in its inner peripheral face, a female thread which is engageable with a male thread formed in an outer peripheral face of the container body. In association with a tightening (screwing) operation of the cap relative to the container body, the conical projection of the liquid discharge plug is caused to advance for penetrating the sealed liquid outlet to allow discharge of the liquid for use. Further, at mutually opposing portions of the liquid discharge plug and the container body respectively, there is provided anti-withdrawal means for preventing loosening rotation of the liquid discharge plug when the liquid discharge plug has been tightened relative to the container body to a predetermined set position (e.g. Japanese utility model registration gazette No. 2560817).

In the case of (1), the factory-sealed liquid outlet is opened up by means of penetration thereof by the conical projection formed in the cap by utilizing the tighten-attachment operation of the cap on to the container body. Unless the cap is tightened properly to the predetermined set position relative to the container body, the amount of penetration of the projection into the liquid outlet of the container body will be insufficient, whereby a smaller aperture than desired will be formed in the liquid outlet, leading to difficulty in discharging operation of the liquid from the container body.

Similarly, in the cases of (2) and (3), the factory-sealed liquid outlet is opened up by means of penetration thereof by the conical projection formed in the liquid discharge plug by utilizing the screw-attachment operation of the plug on to the container body. Unless the plug is tightened properly to the predetermined set position relative to the container body, the amount of penetration of the projection into the liquid outlet of the container body will be insufficient, whereby a smaller aperture than desired will be formed in the liquid outlet, leading to difficulty in discharging operation of the liquid from the container body.

That is to say, in all of the conventional container constructions (1)–(3), unless the cap or plug is tightened or tightened properly to a predetermined set position on the container body, the container, when unsealed for use, will be unable to provide its full liquid discharging performance.

In addition, in all of (1)–(3), in order to prevent further tightening or tightening movement of the cap or plug relative to the container body once the former has reached the predetermined set position, the terminal end of the tightenable range of the cap or plug relative to the container body is set at the predetermined set position. However, for penetrating and opening up the liquid outlet of the container body, a significant force is needed. Then, if such great force is continuously applied after arrival of the cap or plug at the predetermined set position, the cap or plug will be forcibly tightened and twisted relative to the container body. As a result, one or both of the female thread of the container body and male thread of the cap or plug may be deformed or even broken.

Moreover, in the case of (1), in the course of the tightening operation of the cap relative to the container body, the cap is subjected to a significant reaction force from the penetrating operation into the liquid outlet of the container body, whereby the axis of the female thread of the cap tends to be inclined relative to the axis of the male thread of the container body. If the cap is forcibly advanced with such axial inclination to the predetermined set position, the orientation of the resultant aperture formed in the liquid outlet too will be inclined. As a result, the direction of liquid discharged from this unsealed container body will be different from a predetermined discharging direction.

With the constructions of (2) and (3), the liquid discharge plug is un-withdrawably retained at the predetermined set position of the container body with the projection of the former being kept penetrated into the liquid outlet of the latter. Therefore, communication between the inside of the container body and the outlet of the plug may be reliably maintained via the discharge passage formed in the projection or needle. Further, the discharging direction of the liquid from the container body may be restricted by means of the discharge passage and also the un-withdrawable attachment of the plug to the container body too may be effected easily with the series of operation steps described above.

However, if the container body, liquid discharge plug and the cap are to be shipped from the factory as separate components, the packing will be bulky. Further, before putting these into use, a troublesome assembly operation is needed on the side of the user, including the step of tightening the plug on the cap and the further step of attaching the cap to the plug. For this reason, it is desired to have the container body, plug and cap pre-assembled at the factory.

In this case, the liquid discharge plug will have to be temporarily, i.e. loosely tightened on the container body at a predetermined tightening position before the needle formed on the former is penetrated into the liquid outlet of the latter; and then the cap is attached to this plug. However, under such temporarily tightened condition, it is not readily possible to judge from the outside of the container whether the liquid outlet of the container body is unsealed or not. Moreover, with most of containers in general, the cap is to be turned in the loosening (unscrewing) direction for opening the container. Then, even if an instruction note is attached to the container, there is the possibility that the user, due to his/her carelessness or misunderstanding, may erroneously operate the liquid discharge plug (in the case of (2)) or the cap (in the case of (3)) in the opposite, i.e. loosening direction.

With such erroneous operation above, the plug and/or the cap may be detached from the container body. When the user first notices the error by finding the still sealed condition of the liquid outlet, he/she will have to re-attach the plug to the container body by a tightening operation. Then, the initial object of facilitating user's handling of the container will not be achieved. Also, if the user fails to notice the sealed condition of the outlet, he/she may try to open the outlet by means of a needle or similar tool prepared by him/herself; and if this needle or tool is not properly sterilized, the liquid outlet may be contaminated with microorganisms.

The present invention attends to the above-described states of the art, and its primary object is to provide an improved sealed container in which a factory-sealed liquid outlet of a container body can be unsealed in reliable, easy and unmistakable manner by means of penetration thereof by a needle provided to a liquid discharge plug with utilization of a loosening (unscrewing) operation of a cap without forcible tightening (screwing) operation thereof relative to the container body.

SUMMARY OF THE INVENTION

For accomplishing the above-noted object, according to the essential spring of the present invention, a sealed container comprises:

- a container body storing liquid therein and having a sealed liquid outlet;
- a cap which can be detachably screwed on the container body;
- a liquid discharge plug fitted within the cap, the plug having a needle capable of penetrating the liquid outlet of the container body and a discharge passage communicating between the inside and outside the container body through the needle;
- the sealed liquid outlet being unsealed for allowing access to the liquid stored inside the container body by penetration of the outlet by the needle in association with an operation of the cap relative to the container body;
- anti-withdrawal means provided respectively at mutually opposing portions of the liquid discharge plug and the container body, the anti-withdrawal means being capable of retaining the liquid discharge plug at a predetermined set position against withdrawal of the plug from the container body when the plug has been tightened to said predetermined set position relative to the container body;
- one-way rotation preventing means provided respectively at further mutually opposing portions of the liquid discharge plug and the container body, said one-way rotation preventing means preventing rotation of the liquid discharge plug in a unscrewing direction of the cap while allowing rotation thereof in the screwing direction of the cap when the cap has been tightened to a predetermined screwing position immediately before the needle initiates it penetrating action into the sealed liquid outlet; and
- cam means provided respectively at mutually opposed positions of the discharge plug and the cap for pushing the liquid discharge plug toward the liquid outlet of the container body to the predetermined set position of the anti-withdrawal means in association with the unscrewing operation of the cap under the rotation-restricted state provided by the one-way rotation preventing means.

With the sealed container having the above-described construction, when the container body, liquid discharge plug and the cap are pre-assembled at the factory, the cap fitted with the liquid discharge plug will be temporarily screwed to the container body at the predetermined screwing position immediately before the penetration of the sealed liquid outlet by the needle of the plug. Then, when this container is used first time by a user, the user will rotate in the unscrewing direction the cap set at the predetermined screwing position. With this, since the rotation of the liquid discharge plug in the cap-loosening direction is prevented by the one-way rotation preventing means at this predetermined screwing position, the cam means pushes the liquid discharge plug to the predetermined set position relative to the container body, so that the needle of the plug penetrates and opens up the sealed liquid outlet and communication is established between the inside of the container body and the discharge orifice of the plug via the discharge passage, and also the liquid discharge plug is un-withdrawably retained at the predetermined set position by the anti-withdrawal means.

Moreover, in association with the unscrewing operation of the cap located at the predetermined screwing position, the liquid discharge plug is pushed to the predetermined set position relative to the container body while the needle of the former penetrates into the liquid outlet of the latter. Therefore, the liquid discharge plug may reliably set to the predetermined set position, without the cap being forcibly tightened on the container body.

Accordingly, when the sealed container is to be shipped from the factory, by temporarily tightening the cap fitted with the liquid discharge plug on the container body to the predetermined screwing position relative thereto, the packing of this sealed container may be compact and also handling of the container by the user for using the container for first time may be facilitated. And, in this first use of the container, the factory-sealed liquid outlet of the container body may be unsealed in smooth and reliable manner by means of the needle of the liquid discharge plug.

Preferably, the anti-withdrawal means retains the liquid discharge plug against withdrawal thereof from the container body in the axial direction while allowing relative rotation of the former to the latter.

With this construction, after the liquid discharge plug has been pushed to the predetermined set position relative to the container body, the anti-withdrawal means retains the liquid discharge plug against withdrawal thereof from the container body in the axial direction while allowing relative rotation of the former to the latter. Therefore, when the cap fitted to the container body is unscrewed again, the liquid discharge plug may be rotated (with axial movement thereof being restricted) in unison and in the same direction as the cap, in spite of the function of the cam means provided respectively at the mutually opposed portions of the cap and the plug.

Accordingly, after the attachment of the liquid discharge plug, the cam means does not resist the rotational operation of the cap. As a result, the rotational operation of the cap may be with a small force, in spite of the presence of the cam means.

Preferably, a hole-forming portion of the liquid outlet of the container body is formed arcuately concave toward the inside of the container body.

With this construction, even if there exists some amount of displacement between the leading end of the needle and the center of the liquid outlet when the outlet of the container body is to be penetrated by the needle of the discharge plug, the leading end of the needle may be automatically adjusted to the center of the hole-forming portion of the liquid outlet of the container body by the self-centering function provided by the arcuate concavity of the hole-forming portion.

Although it is conceivable to form flat the hole-forming portion of the liquid outlet of the container body, the above construction is more advantageous for facilitating the position-registering between the leading end of the needle of the liquid discharge plug and the liquid outlet of the container body.

Preferably, the cap forms, in an inner bottom face thereof, an inner-plug projection which can be gaplessly fitted into a discharge passage of the liquid discharge plug.

With this construction, in attaching the liquid discharge plug within the cap, the plug may be temporarily retained at a predetermined position inside the cap, by utilizing the inner-plug projection for sealing the discharge passage of the liquid discharge plug, so that the construction needed for preventing inadvertent detachment may be simplified. Further, misalignment between the tip of the needle of the liquid discharge plug and the center of the liquid outlet of the container body may be restricted.

Still preferably, the cap forms, in the inner bottom face thereof, an outer-plug projection which can be gaplessly fitted on an outer peripheral face of the liquid discharge plug.

With this construction, leakage of the liquid stored inside the container body may be restricted by the outer-plug projection. In addition, this outer-plug projection may be utilized also for temporarily retaining the liquid discharge plug at a predetermined position inside the cap. Further, misalignment between the tip of the needle of the liquid discharge plug and the center of the liquid outlet of the container body may be restricted.

Preferably, the cap forms, in the inner bottom face thereof, an annular projection for fitting on the liquid discharge plug and the liquid discharge plug defines a plurality of ridges which come into pressure-contact with an inner peripheral face of the annular projection when the liquid discharge plug is pressed into the annular projection, so as to un-withdrawably retain the liquid discharge plug with a smaller retaining force than that of the anti-withdrawal means.

With the above construction, as the liquid discharge plug is pressed into the annular projection formed in the inner bottom face of the cap to bring the ridges of the plug into pressure-contact with the inner peripheral face of the annular projection, the cap may be temporarily fixed with a predetermined posture within the cap. Therefore, while the cap fitted with the liquid discharge plug is being tightened to the predetermined screwing position before penetration by the needle of the liquid discharge plug, the above construction may restrict the plug inside the cap from being withdrawn to the side of liquid outlet of the liquid container and inclined thereby to incline the posture of the needle of the plug relative to the pressing direction of the liquid discharge plug.

Namely, if the needle of the liquid discharge plug is inclined, the tip of the needle will tend to slip relative to the liquid outlet to fail to penetrate the outlet. Or, the formed hole tends to be deformed so as to form a gap between the hole and the needle. With the above-described construction, however, inclination of the needle of the liquid discharge plug may be effectively restricted, so as to avoid such inconveniences.

Moreover, the retaining force by the ridges of the plug relative to the inner peripheral face of the annular projection is set smaller than that by the anti-withdrawal means. Hence, after the liquid discharge plug has been pressed to the predetermined set position relative to the container body and un-withdrawably retained at this position by the anti-withdrawal means, the liquid discharge plug may be reliably retained to the container body, thus preventing the plug from being inadvertently detached from the container body together with the cap during detachment of the cap from the container body.

Preferably, the one-way rotation preventing means includes a projection formed in the outer peripheral face of the liquid outlet of the container body and a further projection formed in the inner peripheral face of the liquid discharge plug, said projection being oriented such that its leading end is inclined toward the downstream in the rotational tightening direction of the cap; and said further projection includes a cam face which comes into contact with said projection in association with the rotation of the liquid discharge plug relative to the container body in the cap tightening rotation so as to elastically deform said projection toward the outer peripheral face of the liquid outlet of the container body and includes also an engaging face which comes into contact and engagement with said projection in association with the cap-loosening rotation of the liquid discharge plug relative to the container body so as to prevent further rotation of the liquid discharge plug in this cap-loosening direction.

With the above construction, the elastic flexible deformation of the projection and the cam face of the further projection allows rotation of the liquid discharge plug in the cap-tightening direction. Thus, in comparison with a further conceivable construction in which the one-way rotation preventing means consists of a projection formed in the outer peripheral face at the leading cylindrical end portion of the container body and a further projection formed in the inner peripheral face of the liquid discharge plug and both these projections include inclined faces which can ride across each other in association with the rotation of the liquid discharge plug in the cap-loosening direction and engaging faces which can be engaged with each other in association with the same, the above construction is more advantageous for alleviating the force needed for rotating the liquid discharge plug in the cap-tightening direction. So that, the screwing operation of the cap from the predetermined screwing position may be effected easily.

Preferably, the cam means includes a mating pair of inclined faces formed integrally with the inner peripheral face of the cap and with the outer peripheral face of the liquid discharge plug, respectively, said inclined faces sliding and rotating relative to each other in association with the loosening operation of the cap relative to the liquid discharge plug whose rotation is restricted by the one-way rotation preventing means, so as to press the liquid discharge plug into the container body.

With the above construction, the cam means consists essentially of the pair of inclined faces respectively formed integrally with the inner peripheral face of the cap and the outer peripheral face of the liquid discharge plug. Therefore, in comparison with a further conceivable construction in which the cam means consists of separate elements to be assembled respectively with the cap and the liquid discharge plug, the above construction is more advantageous for reducing the number of components and facilitating assembly operation of the container. Consequently, the sealed container may be produced at lower costs.

Further and other objects, features and advantages of the invention will become apparent from the following detailed description of the preferred embodiments thereof with reference to the accompanying drawings.

BRIEF DESCRIPTION OF THE DRAWINGS

FIG. 2 shows the container according to the first embodiment, FIG. 2(a) being a section view showing a condition before a cap is attached to a container body, FIG. 2(b) being an enlarged view showing a tip of a needle, FIG. 2(c) being a section view showing a condition when the cap has been attached and tightened to a predetermined screwing position relative to the container body, FIG. 3 illustrates an operation of rotating the cap in an loosening direction relative to the container body from the predetermined screwing position, FIG. 3(a) being a section illustrating a rotation-prevented condition of a liquid discharge plug in the loosening direction of the cap realized by one-way rotation preventing means, FIG. 3(b) being a section showing a condition in which the cap is being rotated in the loosening direction from the predetermined screwing position relative to the container body, FIG. 3(c) being a section showing a further condition in which the liquid discharge plug has been pressed to a predetermined set position, FIG. 4 illustrates a further operation for further rotating the cap in the tightening direction relative to the container body from the predetermined screwing position, FIG. 4(a) being a section showing a condition in which the one-way rotation preventing means allows rotation of the liquid discharge plug in the tightening (screwing) direction of the cap, FIG. 4(b) being a second showing a further condition in which the liquid discharge plug has been screwed to the predetermined screwing positon.

DESCRIPTION OF THE PREFERRED EMBODIMENTS

Preferred embodiments of the present invention will now be described with reference to the accompanying drawings.

first embodiment

FIGS. 1–5 show a sealed container according to a first embodiment of the present invention. This sealed container includes a container body 3 provided as a hollow mold tube containing a predetermined amount of eye drops 1, an example of liquid, in a sealed state, and having a liquid outlet 2 sealed integrally therewith, a cap 4 in the form of a cylindrical member with a bottom and detachably screwed on the container body 3, and a liquid discharge plug 5. The liquid discharge plug 5 includes a needle 6 capable of penetrating the liquid outlet 2 of the container body 3 and a discharge passage 7 communicating between the inside and outside the container body 3 via the needle 6.

Figure 1:
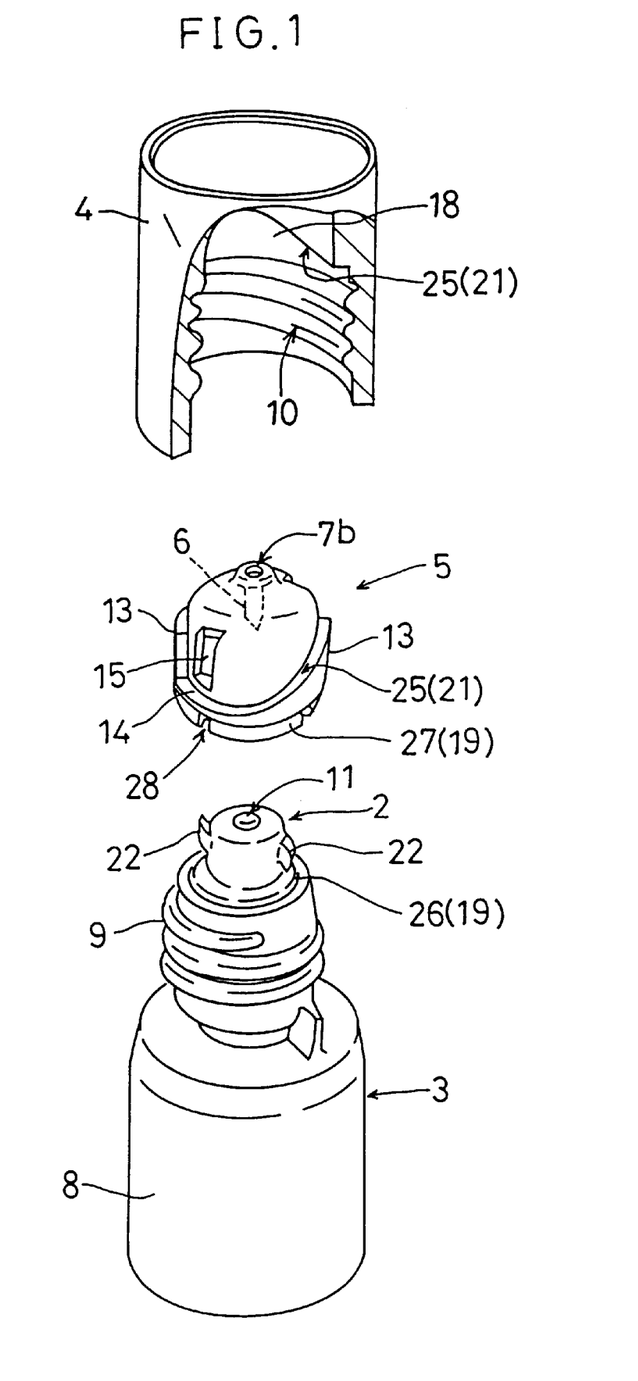
FIG. 1 is a partially cutaway exploded perspective view showing a sealed container according to a first preferred embodiment of the present invention.

As shown in FIGS. 1 and 2, the container body 3 includes a liquid storage section 8 in the form of a cylindrical member having a bottom, a cylindrical female thread 9 engageable with a male thread 10 formed integrally in an inner peripheral face of the cap 4, and the liquid outlet 2 in the form of a cylindrical member with a reduced diameter. And, this container body 3 is integrally formed of synthetic resin (e.g. polyethylene) with the above-mentioned parts thereof.

The liquid outlet 2 of the container body 3 includes a hole-forming portion 11 to be penetrated by the needle 6 of the liquid discharge plug 5, which portion 11 is formed arcuately concave toward the inside of the container body 3 and has a smaller thickness than the rest of the outlet 2.

Incidentally, as one conceivable method of sealing the liquid 1 inside the container body 3, the liquid storage section 8 and the other portions of the liquid container 3 may be formed by the well-known blow molding method. After a predetermined amount of eye drops 1 is introduced into this blow-molded liquid storage section 8, the opening of the molded section 8 will be closed with the remaining portion of the container body 3 and bonded integrally therewith.

Figure 2A:
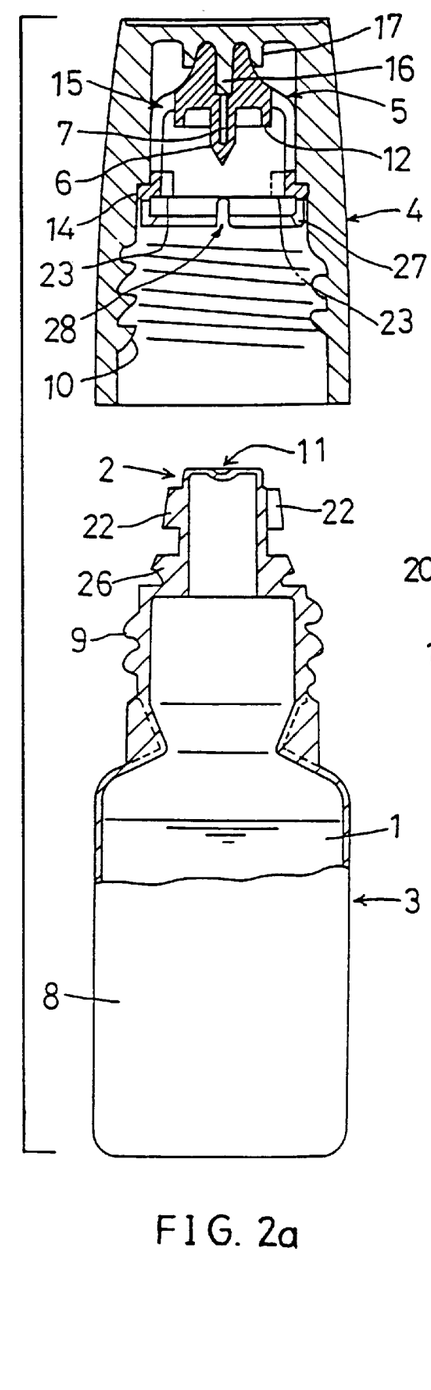
Figure 2B:
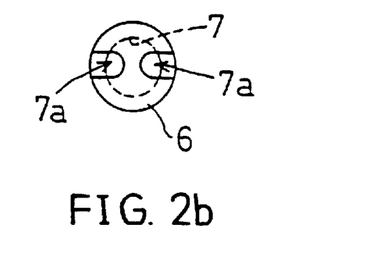
Figure 3A:
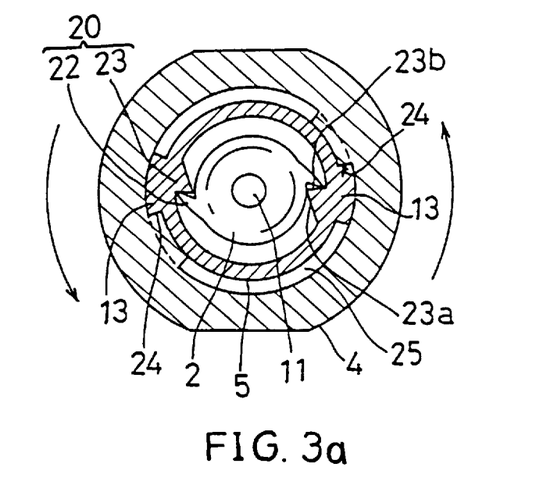

The liquid discharge plug 5 is provided as a cylindrical member with a bottom which can be loosely fitted on the liquid outlet 2 of the container body 3. As shown in FIG. 3(a), this plug 5 includes the needle 6 at the center of its inner bottom face and an annular projection 12 which can be gaplessly placed on a leading end peripheral edge of the liquid outlet 2. As shown in FIG. 2(b), the other face of the discharge plug 5 away from the needle 6 is formed semi-spherically convex with a prominent center. Inlet orifices 7a of the discharge passage 7 are formed at two opposed positions at the leading end of the needle 6; and as shown in FIG. 1, an outlet orifice 7b of the discharge passage 7 is formed at the leading end of the bottom outer face of the liquid discharge plug 7.

The liquid discharge plug 5, needle 6 and the projection 12 are formed of a synthetic resin (e.g. polypropylene, high-density polyethylene,) harder than the synthetic resin forming the container body 3.

Figure 3B:
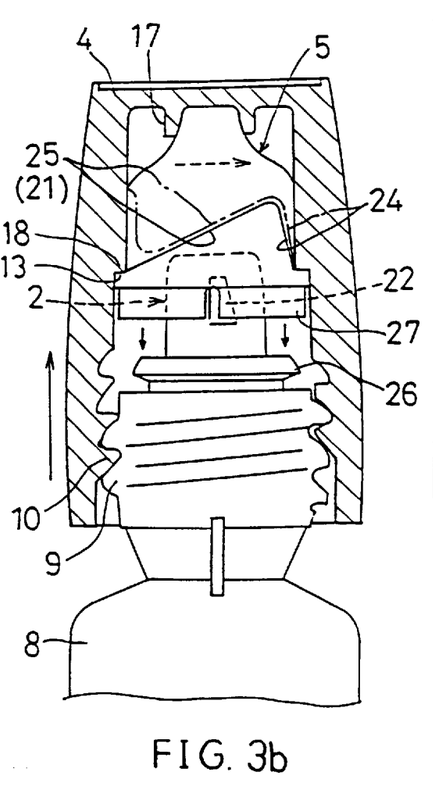

Further, in the outer peripheral face of the liquid discharge plug 5, there are formed a pair of convex portions 13 with an approximate 180 degree phase difference therebetween. As shown in FIGS. 1 and 3(b), when seen in the side view, each convex portion 13 has a substantially triangular configuration having an apex thereof adjacent the outlet orifice 7b. At the end of the opening side of the discharge plug 5, there is integrally formed a large-diameter annular portion 14.

Incidentally, holes 15 formed at two peripheral portions of the plug 5 are holes for withdrawing the mold used for molding the plug 5.

The cap 4 is formed of a synthetic resin (e.g. polypropylene or high-density polyethylene). As shown in FIG. 2(a), this cap 4 integrally forms the female thread 10 in the inner peripheral face thereof and also integrally forms, in the inner bottom face thereof, an inner-plug projection 16 in the form of a pin to be gaplessly fitted within the discharge passage 7 of the plug 5 from the outlet side thereof and an outer-plug annular projection 17 which can be gaplessly fitted on the outer peripheral face of the outer-plug projection 17. The inner-plug projection 16 has a greater projecting amount than the outer-plug projection 17.

Figure 2C:
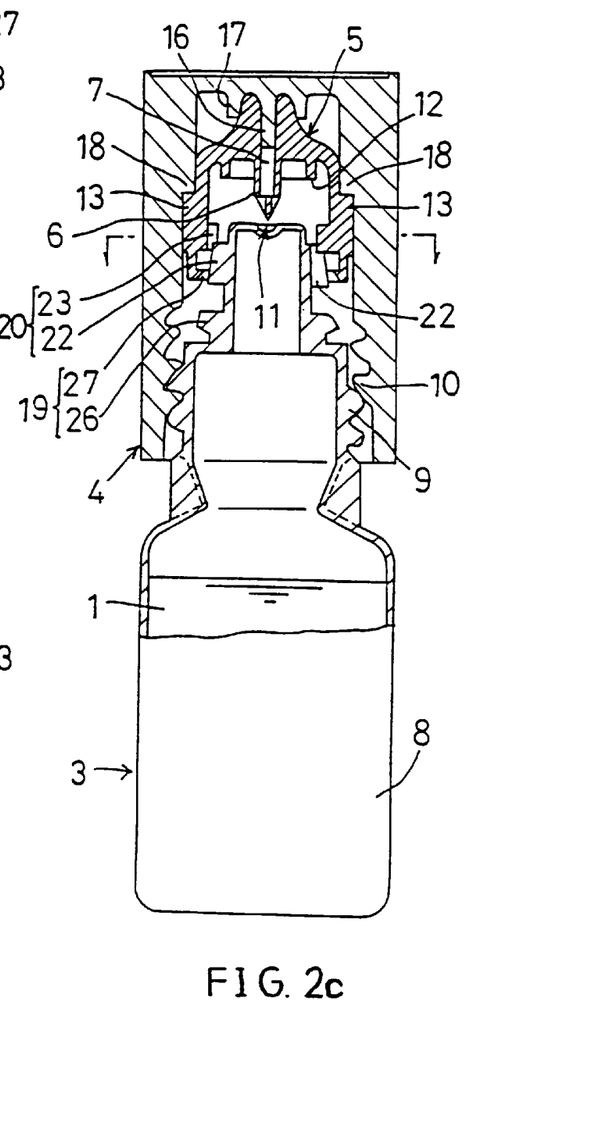

As shown in FIG. 2(c), the inner peripheral face of the cap 4 further defines a pair of concave portions 18 which can be engaged respectively with the convex portions 13 formed in the outer peripheral face of the discharge plug 5 along the rotational axis of the cap 4.

Referring to the assembled state of the sealed container, as shown in FIG. 2(a), the liquid discharge plug 5 is fitted in the cap 4, with the convex and concave portions 13, 18 being engaged with each other, the outer-plug projection 7 being detachably fitted on the outlet peripheral edge of the discharge plug 5. Then, as shown in FIG. 2(c), within the screwable stroke of the cap 4 relative to the container body 3, the cap 4 will be tightened to a predetermined screwing position before the needle 6 initiates its penetration. From this position, the cap 4 will be turned reverse in the loosening (unscrewing) direction (direction shown in FIG. 3(a)). In association with this operation, the needle 6 of the liquid discharge plug 5 will advance to penetrate into the hole-forming portion 11 of the liquid outlet 2 of the container body 3 downwardly in FIG. 3.

As shown in FIGS. 1–4, at mutually opposed positions of the discharge plug 5 and the container body 3, there is respectively provided anti-withdrawal means 19 (26, 27) for retaining the plug 5 at a predetermined set position against withdrawal thereof when the penetration, i.e. opening of the hole-forming portion 11 of the liquid outlet 2 of the container body 3 by means of the needle 6 of the plug 5 has been completed. Then, after the plug 5 is un-withdrawably retained to the container body 3 by the anti-withdrawal means 19, the plug 5 is prevented from being detached or withdrawn from the container body 3. That is to say, under this condition, the cap 4 alone can be removed from the container body 3 by an unscrewing operation of the former relative to the latter.

At further mutually opposed positions of the discharge plug 5 and the container body 3, there is respectively provided one-way rotation preventing means 20 (22, 23) for preventing rotation of the liquid discharge plug 5 in the loosening direction of the cap 4 while allowing rotation thereof in the tightening direction of the cap 4 when the cap 4 has been tightened to the above-described predetermined screwing position immediately before the needle 6 initiates its penetrating action.

At still further mutually opposed positions of the discharge plug 5 and the container body 3, there are provided cam means 21 (25) for pushing the liquid discharge plug 5 toward the storage section 2 of the container body 3 to the predetermined set position of the anti-withdrawal means 19 in association with the loosening (unscrewing) operation of the cap 4 under the rotation-restricted state provided by the one-way rotation preventing means 20 (22, 23).

Figure 4A:
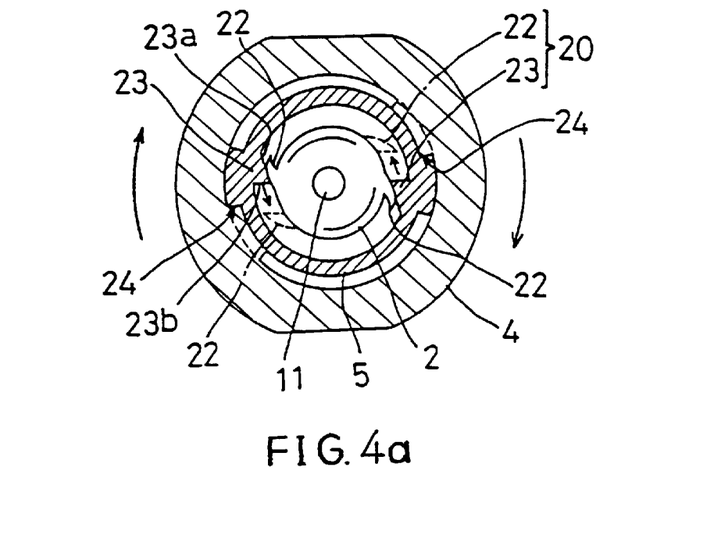

As shown in FIG. 3(a) and FIG. 4(a), the one-way rotation preventing means 20 includes a pair of projections 22 disposed with substantially 180 phase difference therebetween and formed integrally with the outer peripheral face of the container body 3 and a pair of farther projections 23 disposed with substantially 180 phase difference therebetween and formed integrally with the inner peripheral face of the liquid discharge plug 5. Each projection 22 is oriented such that its leading end is inclined toward the downstream in the rotational tightening direction of the cap 4.

Further, as shown in FIG. 4(a), each further projection 23 includes a cam face 23a which comes into contact with the corresponding projection 22 in association with the rotation of the plug 5 relative to the container body 3 in the cap tightening rotation so as to elastically deform the projection 22 toward the outer peripheral face of the liquid outlet 2 of the container body 3 and an engaging face 23b which comes into contact and engagement with the projection 22 in association with the cap-loosening rotation of the plug 5 relative to the container body 3 so as to prevent further rotation of the plug 5 in this cap-loosening direction.

As shown in FIG. 3, the cam means 21 consists essentially of a mating pair of inclined faces 25 formed integrally with the concave portions 18 provided in the inner peripheral face of the cap 4 and with the convex portions 13 provided in the outer peripheral face of the liquid discharge plug 5, respectively. These inclined faces 25 slide and rotate relative to each other in association with the loosening operation of the cap 4 relative to the liquid discharge plug 5 whose rotation is restricted in the above-described manner by the one-way rotation preventing means 20. That is, these inclined faces 25 are formed respectively of one inner side face of the convex portion 13 having substantially triangular configuration in the side view and of one inner side face the concave portion 18 which comes into contact therewith.

Further, each concave portion 18 formed in the inner peripheral face of the cap 4 and each convex portion 13 formed in the outer peripheral face of the liquid discharge plug 5 respectively include an engaging face 24 for rotating the plug 5 together with the cap 4 in association with the tightening (screwing) operation of the cap 4. And, these engaging faces 24 are formed so as to extend substantially along the rotational axis of the cap. That is, these inclined faces 24 are formed respectively of the other inner side face of the convex portion 13 having substantially triangular configuration in the side view and of the other inner face the concave portion 18 which comes into contact therewith.

As shown in FIG. 2, the anti-withdrawal means 19 includes an engaged portion 26 in the form of annular projection provided at the base end of the liquid outlet 2 of the container body 3 and an engaging pawl 27 which is formed integral with a leading end peripheral edge of the large-diameter annular portion 14 formed integrally with the discharge plug 5 and which elastically comes into engagement with the engaged portion 26 while allowing relative rotation of the discharge plug 5 when the plug 5 has been pressed to a predetermined set position relative to the container body 3.

Namely, as shown in FIG. 2, the anti-withdrawal means 19 retains the liquid discharge plug 5 against withdrawal of the plug 5 from the container body 3 in the axial direction while allowing relative rotation of the former to the latter.

Incidentally, at four peripheral portions of the large-diameter annular portion 14, there are defined cutouts 28 for allowing movement of this large-diameter annular portion 14 in the radially expending direction when the engaging pawls 27 come into engagement with the engaged portions 26.

With the sealed container having the construction detailed above, the liquid discharge plug 5 will be fitted inside the cap so that the inner-plug projection 16 is fitted inside the discharge passage 7 of the liquid discharge plug 5 and also the outer-plug projection 17 is fitted on the outlet peripheral edge of the discharge passage 7 of the discharge plug 5; then, the cap 4 will be temporarily tightened to the predetermined screwing position relative to the container body 3. Under this temporarily tightened condition, the container is ready for shipment.

Incidentally, in this embodiment, the predetermined screwing position can be specifically defined as follows. Namely, within the screwable range of the cap 4 relative to the container body 3, this predetermined screwing position is provided as such a position where before penetration of the hole-forming portion 11 by the needle 6 of the discharge plug 5, the liquid discharge plug 5 can be retained under a condition in which the needle 6 of the plug 5 fitted within the cap 4 is located immediately before the hole-forming portion 11 and portions of the projections 22, 23 constituting the one-way rotation preventing means 20 are overlapped with each other in the peripheral direction of the discharge plug 5.

Figure 3C:
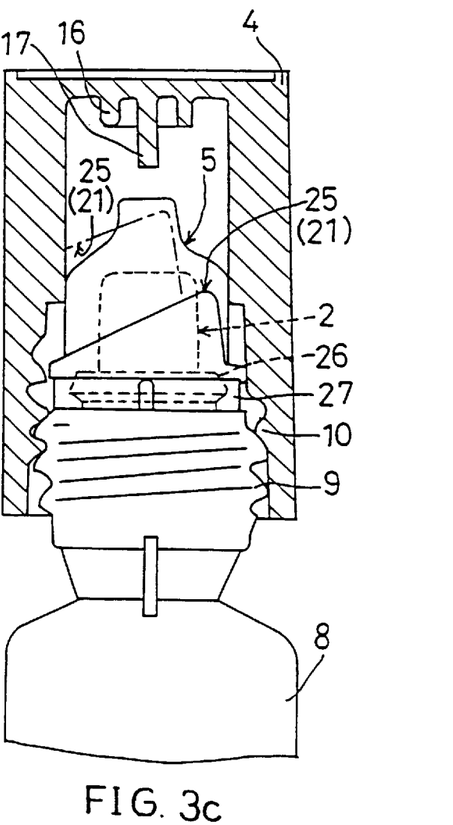

Then, as illustrated in FIGS. 3(a), (b) and (c), when a user of the eye medicine liquid 1 loosens or unscrews the cap 4 which is temporarily retained at the predetermined screwing position as originally shipped from the factory, the one-way rotation preventing means 20 prevents rotation of the plug 5 in the cap loosening direction, so that the inclined faces 25 constituting the cam means 21 begin to slide and rotate relative to each other. In association therewith, a pressing force is applied to the discharge plug 2 toward the container body 3 and the plug 5 is moved toward the liquid outlet 2 of the container body 3 to cause the needle 6 of the plug 5 to penetrate and open up the factory-sealed liquid outlet 2; and also when the discharge plug 5 has reached the predetermined set position, the plug comes into engagement with the anti-withdrawal means 19, thereby to complete this unsealing operation of the liquid outlet 2 of the container body 3 utilizing the movement of the needle 6 of the discharge plug 5 in association with the rotational operation of the cap 4 in the loosening direction.

Though not shown, in the outer peripheral face of the container body 3 or of the cap 4, there is provided an indicator means such as an arrow for indicating the proper direction of the rotational operation of the cap 4, which is to be effected when the container is used for the first time, for allowing the liquid outlet 2 of the container body 3 to be penetrated by the needle 6 of the plug 5 in association with the unscrewing operation of the cap 4.

Incidentally, according to the general spirit of the present invention, by utilizing the cam means 21, in association with the rotational operation of the cap 4 in the loosening direction, the liquid discharge plug 5 is pushed toward the liquid outlet 2 of the container body 3 and also the needle 6 of this pushed plug 5 is caused to penetrate and unseal the factory-sealed liquid outlet 2. In the case of the construction of this particular embodiment, however, with a rotation operation of the cap 4 in the opposite direction, i.e. tightening direction too, the plug 5 is pushed toward the liquid outlet 2 of the container body 3 and the liquid outlet 2 can be opened by means of the needle 6 of this plug 5.

Figure 4B:
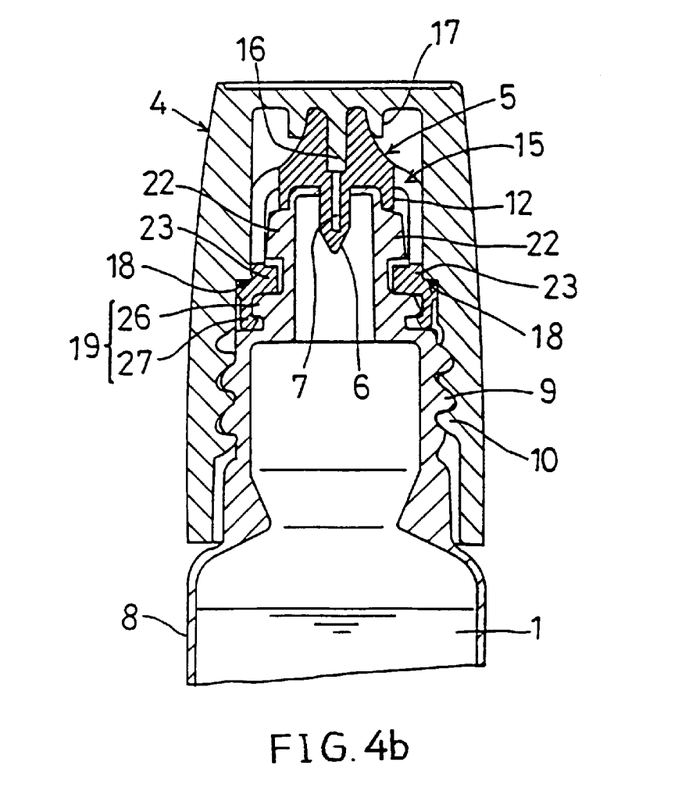
Figure 5:
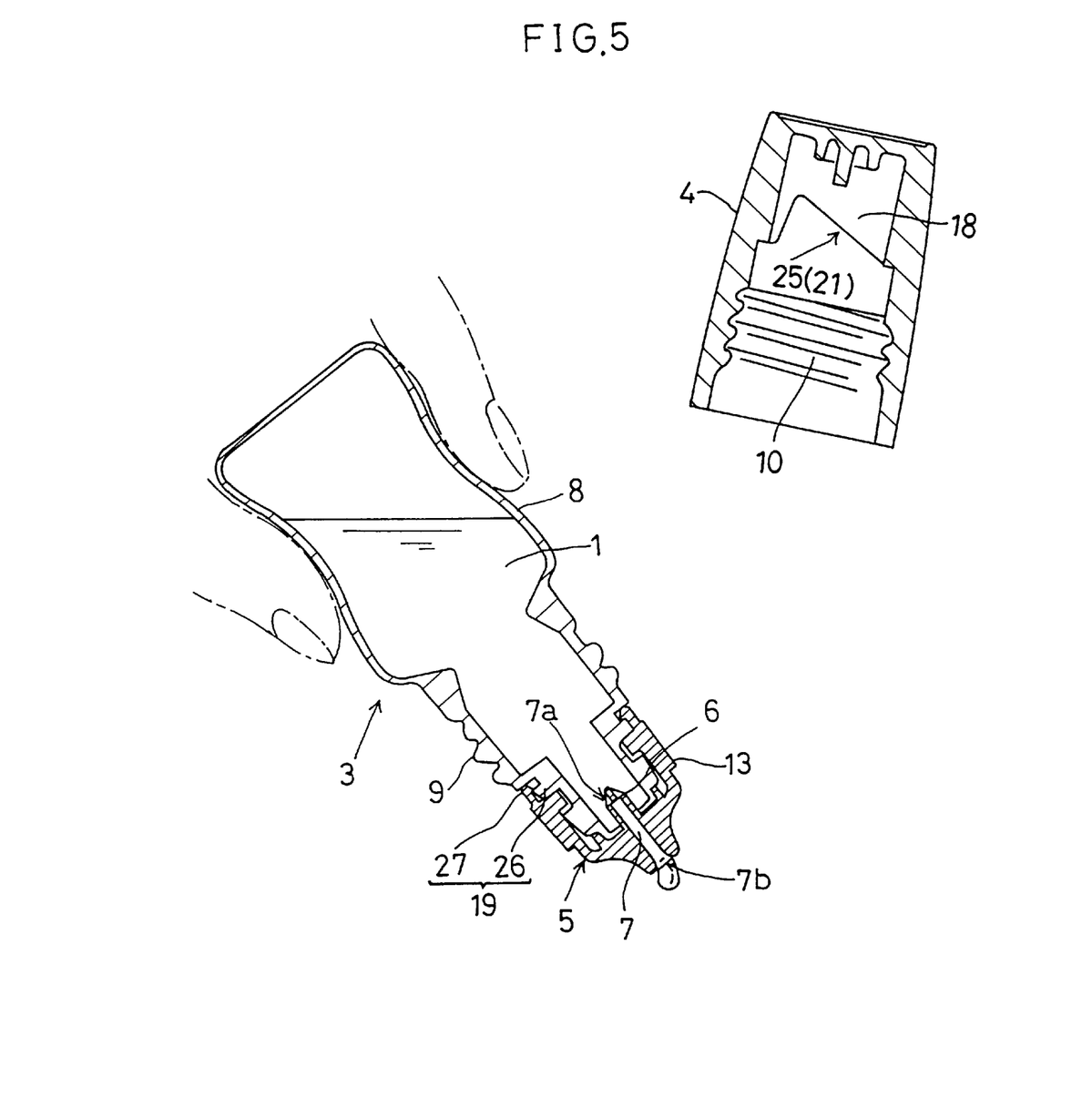
FIG. 5 is a section view showing in-use condition of the container.

Specifically, as shown in FIGS. 4(a), (b), if the user rotates the cap 4, which is temporarily tightened to the predetermined screwing position, in the tightening direction, the engaging faces 24 adapted for rotating the plug 5 and the cap 4 in the cap tightening direction come into contact with each other, so that the plug 5 rotates together with the cap 4 toward the liquid outlet 2 of the container body 3 and then the needle 6 of the plug 5 penetrates the hole-forming portion 11 of the liquid outlet 2 of the container body 3, and also when the cap 4 is further screwed until the plug 5 reaches the predetermined set position, the plug comes into engagement with the anti-withdrawal means 19, thereby to complete this unsealing operation of the liquid outlet 2 of the container body 3 utilizng the movement of the needle 6 of the discharge plug 5 in association with the reverse rotational operation of the cap 4 in the tightening direction.

After the liquid outlet 2 of the container body 3 has been unsealed, the outlet orifice 7b of the liquid discharge plug 5 may be closed by screw-fitting the cap 4 on the container body 3. Under this condition, the concave and convex portions 13, 18 are engaged with each other, the inner-plug projection 16 of the cap 4 is fitted within the discharge passage 7 of the liquid discharge plug 5, and also the outer-plug projection 17 of the cap 4 is fitted on the outlet peripheral edge of the discharge passage 7 of the plug 5.

second embodiment

Figure 6:
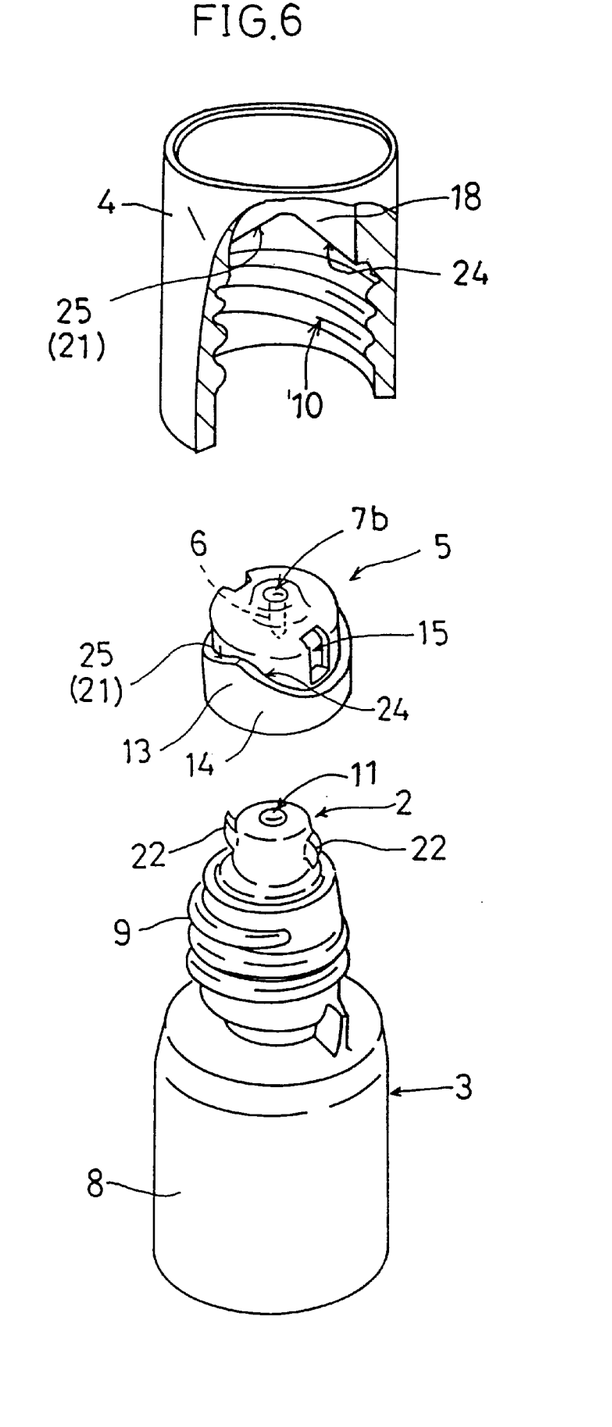
FIG. 6 is a partially cutaway exploded perspective view showing a sealed container according to a second preferred embodiment of the present invention.

FIG. 6 shows a modified sealed container according to a second embodiment of the invention. In this embodiment, the engaging faces 24 for rotating the liquid discharge plug 5 together with the cap 4 in the cap tightening direction are formed as inclined faces having the opposite inclination to that of the inclined faces 25 constituting the cam means 21.

The rest of the construction of this embodiment is identical to the first embodiment. Hence, those components having identical constructions or functions are denoted with identical reference numerals and marks and will not be described here.

third embodiment

Figure 7:
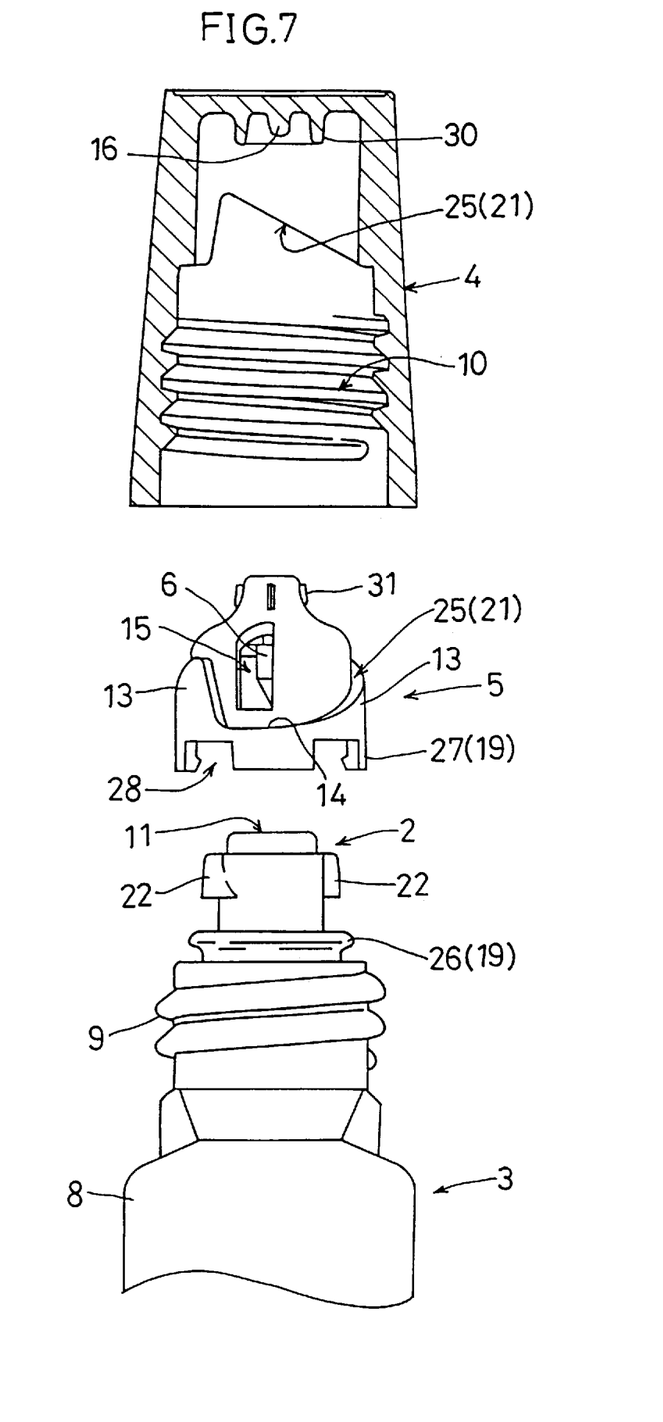
FIG. 7 is a partally cutaway exploded perspective view showing a sealed container according to a third preferred embodiment of the present invention.
Figure 8:
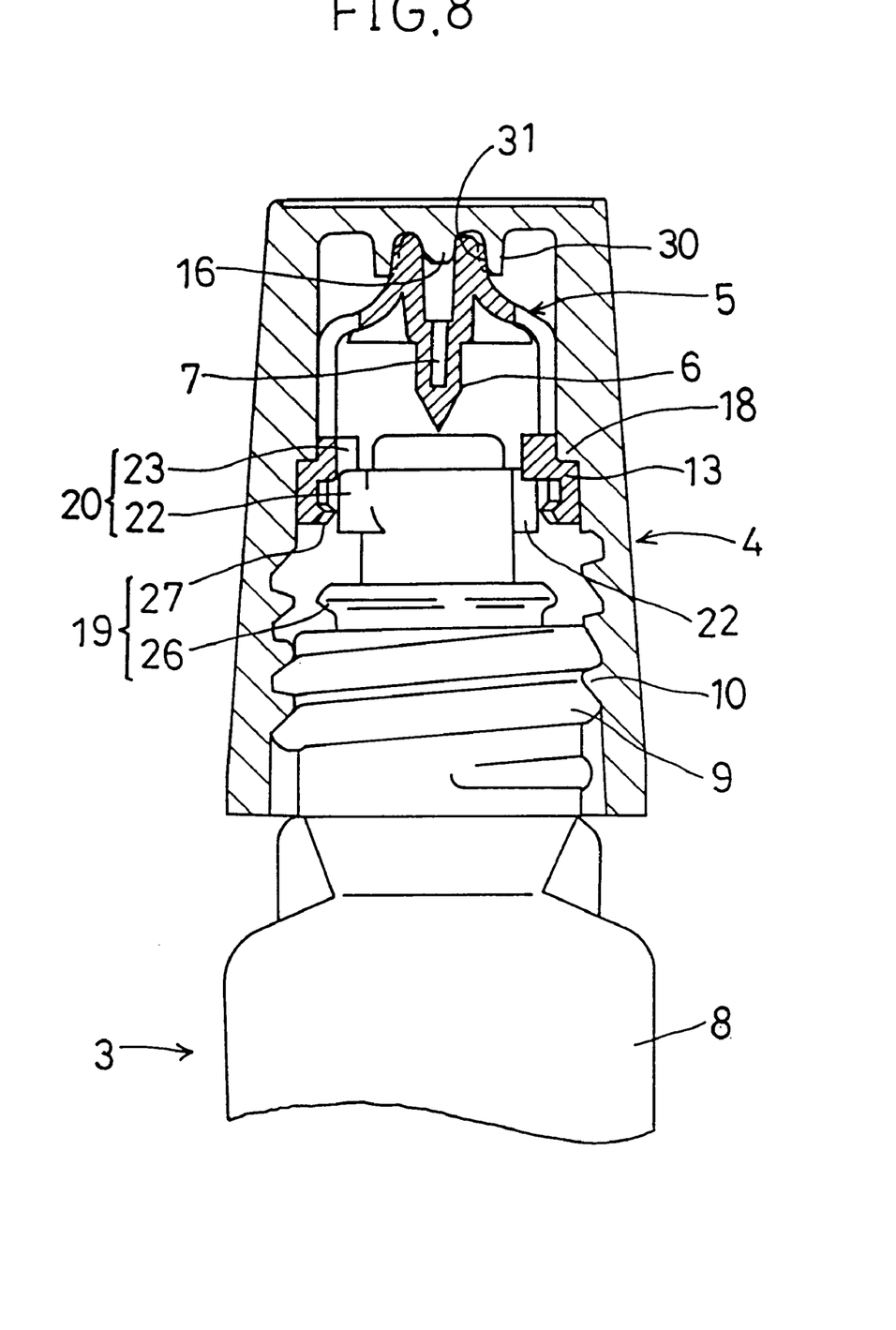
FIG. 8 is a section view showing a condition of the container in which the cap has been tightened or screwed to the predetermined screwing position relative to the container body.

FIGS. 7 and 8 show a still modified sealed container according to a third embodiment of the present invention. In this case, in the inner bottom face of the cap 4, there are integrally formed an inner-plug projection 16 in the form of a pin which can be gaplessly engaged into the discharge passage 7 of the liquid discharge plug 5 from its outlet side and an annular projection 30 which can be engaged outwardly on the outlet peripheral edge of the liquid discharge plug 5.

The inner-plug projection 16 has a smaller projecting amount than the annular projection 30.

Further, at four portions in the outer peripheral face of the outlet peripheral edge of the liquid discharge plug 5, there are formed a plurality of ridges 31. When the liquid discharge plug 5 is pressed into the annular projection 30, the ridges 31 come into pressure-contact with the inner peripheral face of this annular projection 30 so as to un-withdrawably retain the plug 5 with a retaining force smaller than that of the anti-withdrawal means 19.

The rest of the construction of this embodiment is identical to the first embodiment. Hence, those components having identical constructions or functions are denoted with identical reference numerals and marks and will not be described here.

other embodiments (1) In the foregoing embodiments, the one-way rotation preventing means 20 consists essentially of the pair of projections 22 formed in the outer peripheral face of the liquid outlet 2 of the container body 3 and of the pair of projections 23 formed in the inner peripheral face of the liquid discharge plug 5. However, the specific number and positions of these projections 22, 23 are not particularly limited in the present invention, but may vary in many ways depending on the convenience.

(2) In the foregoing embodiments, the inner bottom face of the cap 4 forms the inner-plug projection 16 for gaplessly fitting within the discharge passage of the plug 5 and the outer-plug projection 17 for gaplessly fitting on the plug 5. However, the inner bottom face of the cap 4 may form only either of one or neither of these projections 22, 23.

(3) The cam means 21 may alternatively comprise a combination of an inclined face and a projection which slide and rotate relative to each other in association with the loosening operation of the cap 4 relative to the plug 5 having its rotation restricted by the one-way rotation preventing means 20, so as to apply the pressing force to the liquid discharge plug 5 toward the container body 3.

(4) In the foregoing embodiments, the inner peripheral face of the cap 4 forms the concave portions 18 whist the outer peripheral face of the liquid discharge plug 5 forms the convex portions 13. Conversely, it is also possible to form the convex portions 13 in the inner peripheral face of the cap 4 and the concave portions 18 in the outer peripheral face of the liquid discharge plug 25.

(5) In the foregoing embodiments, eye medicine liquid is employed as the liquid stored and sealed in the container body 3. However, the kind of liquid is not limited thereto. The liquid may be e.g. liquid medicine for otorhinilogical treatment.

The present invention may be embodied in other specific forms without departing from the spirit or essential characteristics thereof. The present embodiments are therefore to be considered in all respects as illustrative and not restrictive, the scope of the invention being indicated by the appended claims rather than the foregoing description and all changes which come within the meaning and range of equivalency of the claims are therefore intended to be embraced therein.

What is claimed is:

1. A sealed container comprising:

a container body storing liquid therein and having a sealed liquid outlet;

a cap which can be detachably screwed on the container body;

a liquid discharge plug fitted within the cap, the plug having a needle capable of penetrating the liquid outlet of the container body and a discharge passage communicating between an inside and an outside of the container body through the needle, the sealed liquid outlet being unsealed for allowing access to the liquid stored inside the container body by penetration of the outlet by the needle in association with an operation of the cap relative to the container body;

anti-withdrawal means provided respectively at mutually opposing portions of the liquid discharge plug and the container body, the anti-withdrawal means being capable of retaining the liquid discharge plug at a predetermined set position against withdrawal of the plug from the container body when the plug has been tightened to said predetermined set position relative to the container body;

one-way rotation preventing means provided respectively at further mutually opposing portions of the liquid discharge plug and the container body, said one-way rotation preventing means preventing rotation of the liquid discharge plug in an unscrewing direction of the cap while allowing rotation thereof in a screwing direction of the cap when the cap has been tightened to a predetermined screwing position immediately before the needle penetrates into the sealed liquid outlet; and cam means provided respectively at mutually opposed positions of the discharge plug and the cap for pushing the liquid discharge plug toward the liquid outlet of the container body to the predetermined set position of the anti-withdrawal means in association with the unscrewing operation of the cap under the rotation-restricted state provided by the one-way rotation preventing means.

2. The container according to claim 1, wherein the cap forms, in an inner bottom face thereof, an outer-plug projection which can be gaplessly fitted on an outer peripheral face of the liquid discharge plug.

3. The container according to claim 1, wherein the cap forms, in an inner bottom face thereof, an annular projection for fitting on the liquid discharge plug and the liquid discharge plug defines a plurality of ridges which come into pressure-contact with an inner peripheral face of the annular projection when the liquid discharge plug is pressed into the annular projection, so as to prevent the withdrawal of the liquid discharge plug with a smaller retaining force than that of the anti-withdrawal means.

4. The container according to claim 1, wherein the one-way rotation preventing means includes a projection formed in an outer peripheral face of the liquid outlet of the container body and a further projection formed in an inner peripheral face of the liquid discharge plug, said projection being oriented such that its leading end is inclined toward the downstream in the rotational tightening direction of the cap; and said further projection includes a cam face which comes into contact with said projection in association with the rotation of the liquid discharge plug relative to the container body in the cap tightening rotation so as to elastically deform said projection toward the outer peripheral face of the liquid outlet of the container body and further includes an engaging face which comes into contact and engagement with said projection in association with the cap-loosening rotation of the liquid discharge plug relative to the container body so as to prevent further rotation of the liquid discharge plug in the cap-loosening direction.

5. The container according to claim 1, wherein the cam means includes a mating pair of inclined faces formed integrally with an inner peripheral face of the cap and with an outer peripheral face of the liquid discharge plug, respectively, said inclined faces sliding and rotating relative to each other in association with the loosening operation of the cap relative to the liquid discharge plug whereby rotation of the liquid discharge plug is restricted by the one-way rotation preventing means so as to press the liquid discharge plug into the container body.

6. The container according to claim 1, wherein the cap forms, in an inner bottom face thereof, an inner-plug projection which can be gaplessly fitted into a discharge passage of the liquid discharge plug.

7. The container according to claim 6, wherein the cap forms, in the inner bottom face thereof, an outer-plug projection which can be gaplessly fitted on an outer peripheral face of the liquid discharge plug.

8. The container according to claim 1, wherein a hole-forming portion of the liquid outlet of the container body is formed arcuately concave toward the inside of the container body.

9. The container according to claim 8, wherein the cap forms, in an inner bottom face thereof, an inner-plug projection which can be gaplessly fitted into a discharge passage of the liquid discharge plug.

10. The container according to claim 8, wherein the cap forms, in an inner bottom face thereof, an outer-plug projection which can be gaplessly fitted on an outer peripheral face of the liquid discharge plug.

11. The container according to claim 1, wherein the anti-withdrawal means retains the liquid discharge plug against withdrawal thereof from the container body in an axial direction while allowing rotation of the liquid discharge plug relative to the container body.

12. The container according to claim 11, wherein a hole-forming portion of the liquid outlet of the container body is formed arcuately concave toward the inside of the container body.

13. The container according to claim 11, wherein the cap forms, in an inner bottom face thereof, an inner-plug projection which can be gaplessly fitted into a discharge passage of the liquid discharge plug.

14. The container according to claim 11, wherein the cap forms, in an inner bottom face thereof, an outer-plug projection which can be gaplessly fitted on an outer peripheral face of the liquid discharge plug.

15. The container according to claim 11, wherein the cap forms, in an inner bottom face thereof, an annular projection for fitting on the liquid discharge plug and the liquid discharge plug defines a plurality of ridges which come into pressure-contact with an inner peripheral face of the annular projection when the liquid discharge plug is pressed into the annular projection, so as to prevent the withdrawal of the liquid discharge plug with a smaller retaining force than that of the anti-withdrawal means.

16. The container according to claim 11, wherein the one-way rotation preventing means includes a projection formed in an outer peripheral face of the liquid outlet of the container body and a further projection formed in an inner peripheral face of the liquid discharge plug, said projection being oriented such that its leading end is inclined toward the downstream in the rotational tightening direction of the cap; and said further projection includes a cam face which comes into contact with said projection in association with the rotation of the liquid discharge plug relative to the container body in the cap tightening rotation so as to elastically deform said projection toward the outer peripheral face of the liquid outlet of the container body and further includes an engaging face which comes into contact and engagement with said projection in association with the cap-loosening rotation of the liquid discharge plug relative to the container body so as to prevent further rotation of the liquid discharge plug in the cap-loosening direction.

17. The container according to claim 11, wherein the cam means includes a mating pair of inclined faces formed integrally with an inner peripheral face of the cap and with an outer peripheral face of the liquid discharge plug, respectively, said inclined faces sliding and rotating relative to each other in association with the loosening operation of the cap relative to the liquid discharge plug whereby rotation of the liquid discharge plug is restricted by the one-way rotation preventing means so as to press the liquid discharge plug into the container body.

18. The container according to claim 11, wherein a hole-forming portion of the liquid outlet of the container is formed arcuately concave toward the inside of the container body, and the cap forms, in an inner bottom face thereof, an inner-plug projection which can be gaplessly fitted into a discharge passage of the liquid discharge plug.

19. The container according to claim 11, wherein a hole-forming portion of the liquid outlet of the container body is formed arcuately concave toward the inside of the container body, the cap forms, in an inner bottom face thereof, an outer-plug projection which can be gaplessly fitted on an outer peripheral face of the liquid discharge plug.

20. The container according to claim 11, wherein a hole-forming portion of the liquid outlet of the container body is formed arcuately concave toward the inside of the container body, the cap forms, in an inner bottom face thereof, an inner-plug projection which can be gaplessly fitted into a discharge passage of the liquid discharge passage, and the cap forms, in the inner bottom face thereof, an outer-plug projection which can be gaplessly fitted on an outer peripheral face of the discharge plug.

* * * * *